(12) United States Patent
Edwards et al.

(10) Patent No.: US 6,258,093 B1
(45) Date of Patent: Jul. 10, 2001

(54) SURGICAL REAMER CUTTER

(76) Inventors: Garland U. Edwards, 13742 Village Ridge Dr., Midlothian, VA (US) 23113; William R. Krause, 820 Gilliams Mountain Rd., Charlottesville, VA (US) 22903

( * ) Notice: Subject to any disclaimer, the term of this patent is extended or adjusted under 35 U.S.C. 154(b) by 0 days.

(21) Appl. No.: 09/494,108

(22) Filed: Jan. 28, 2000

Related U.S. Application Data

(60) Provisional application No. 60/118,024, filed on Feb. 1, 1999.

(51) Int. Cl.[7] .................................................... A61B 19/00
(52) U.S. Cl. ................................................ 606/80; 606/85
(58) Field of Search ................................. 606/80, 81, 85, 606/82, 84

(56) References Cited

U.S. PATENT DOCUMENTS

| 569,285 | * | 10/1896 | Jacobs | 606/85 |
|---|---|---|---|---|
| 4,625,725 | | 12/1986 | Davison et al. | 128/304 |
| 4,706,659 | | 11/1987 | Mathews et al. | . |
| 4,751,922 | | 6/1988 | DiPietropolo | . |
| 5,122,134 | | 6/1992 | Borzone | 606/80 |
| 5,342,365 | | 8/1994 | Waldman | 606/85 |
| 5,376,092 | | 12/1994 | Hein et al. | 606/81 |
| 5,755,719 | | 5/1998 | Frieze et al. | 606/81 |
| 5,759,185 | | 6/1998 | Grinberg | 606/80 |

FOREIGN PATENT DOCUMENTS

| 1553078 | 3/1990 | (SU) | A61B/17/16 |
|---|---|---|---|
| WO 90/07908 | 7/1990 | (WO) | A61B/17/16 |

* cited by examiner

*Primary Examiner*—Paul J. Hirsch
(74) *Attorney, Agent, or Firm*—Sheldon H. Parke

(57) ABSTRACT

The invention provides a cutter head that reduces the cutting force and number of reamers required by increasing the depth of cut or cutting length. The cutting head uses at least one tooth placed along the length of flutes formed within the body of the cutting head. The grooves forming the flutes can follow a first helical path along the body length, maintaining a substantially constant path over a major portion of the entire length in relation to the axes or, alternatively, have a constantly changing path. A second pattern can follow a second, contiguous helical path that has a second radial orientation to the axis. The teeth can be formed from a sinusoidal wave form comprised of a continuous radius going from convex to concave, with each of the teeth having a predetermined pitch from the crest to the base. In another embodiment the crest of the teeth on the first flute is offset axially by a predetermined distance from the teeth on the adjacent flutes. The offset can be determined by dividing the pitch on each flute by the number of flutes. The cutting head can, in an alternate embodiment, have a notch within each of the flutes. The notch forms a pair of teeth, the crests of each of the teeth having either a substantially equal radius or a different radius, depending upon the placement of the notch.

15 Claims, 14 Drawing Sheets

SURGICAL REAMER CUTTER

CROSS-REFERENCE TO RELATED PATENT APPLICATION

The present application claims the benefits under 35 U.S.C. 119(e) of provisional patent application Ser. No. 60/118,024 filed Feb. 1, 1999. This application incorporates by reference, as though recited in full, the disclosure of copending provisional application 60/118,024.

BACKGROUND OF THE INVENTION

1. Field of Invention

This invention relates to the reamer cutting head for the surgical reamers used by surgeons during intramedullary reaming and other orthopedic procedures requiring the internal enlargement of bone central canals.

2. Brief Description of the Prior Art

Surgeons have for years used reamers during orthopedic surgery to enlarge intramedullary canals of long bones such as the femur, tibia and humerus. The purpose of this is for sizing or enlarging the canal for the acceptance for an intramedullary fixation device or total joint implant. This fixation device is usually a rod or tube inserted into the correctly sized canal and held in place with screws.

Intramedullary reaming is generally performed with a rotary cutting tool attached to a flexible shaft. Reamer cutting tools are mounted permanently to a flexible shaft or are interchangeable by means of an interlocking dove tail slot.

Prior to the reaming process a wire rod is inserted into the central canal as a guide for the reamer. The reamer and shaft each have an axial bore concentric with the axis of rotation. The reamer is passed over the rod and feed into the canal for enlarging. The canal is enlarged incrementally with a series of reamers, which increase in diameter by 0.5 mm. A separate interchangeable cutter head or complete cutter head/shaft assembly is required for each step. This requires that the reamer be extracted from the canal and slid off the guide wire. The next incremental cutter head or complete cutter head/shaft assembly is then passed over the wire and advanced into the canal. For an intramedullary nail this would entail approximately 9 or 10 interchanges.

The prior art cutting heads have been cylindrical, elliptical, ball or bullet shaped with a plurality of fluted spaced around the axis of rotation. Each flute has a cutting edge formed when a "V" groove is machined along its axis from the front tip to the rear end of the cutter. Generally, straight or helical "V" grooves are machined into the cutter in order to create a rake angle at the leading edge.

This "V" groove also serves as an area for chips and tissue after being cut from the internal surface of the bone canal. Such a cutter head is shown generally in U.S. Pat. No. 4,706,659 (Matthews et. al.) and U.S. Pat. No 4,751,922 (DiPietrolo) as a cutting head on a shaft but does not refer to the design of the cutting head. Borzone et. al. (U.S. Pat. No. 5,122,134) describe a cutting head having a series of circumferentially spaced flutes having a first section extending in a straight line from the leading edge of the cutter, a curved central portion formed as a section of a torus, and a second straight section back to the trailing edge of the cutting head.

The form of the "V" groove machined into the cutter creates the rake angle and cutting edge of the first flute and the trailing edge of the next adjacent flute. By varying this "V" angle and depth with respect to the number of flutes required, a constant circumferential width along the cutting surface is formed. This constant circumferential width generally starts at the front tip and extends to the rear end of the cutter. Each of the flutes has a cutting edge and when rotated, forms the cutting surface of the reamer. This cutting surface has a ground relief angle to enable it to cut freely.

The prior art reamer heads have been concerned with cutter binding in the bone canal and cutter retraction after binding. The general configuration of prior art reamer heads have not addressed the problems of heat generation, cutter force, intramedullary pressure and the quantity of cutter heads required to enlarge the intramedullary canal.

SUMMARY OF THE INVENTION

The invention provides a cutter head which reduces the cutting force. The cutter head increases the depth of cut or cutting length which can be obtained with the reamer head, thus reducing the number of reamers needed during the procedure, reducing hospital inventory cost, and reducing operative time of the procedure.

The invention provides a cutter head which counter acts the tendency of a high helix angle cutter to dig in or cut into the bone without clearing away the produced chips or debris.

The invention provides a cutter bead which reduces the intramedullary pressure ahead of the cutting head and reduce the risk of the patient developing vascular complications resulting from fat embolism.

The invention provides a cutter head that reduces the tendency of cutters to fail to clear chips and debris and to bind up inside the bone canal.

A cutting head for surgical reamers for use in enlarging the bore of the central medullary canal of a bone having a leading tip and a trailing end, connectable to a drive shaft, forming a length. The body has a circumference and at least a pair of flutes, formed by grooves, extending in at least one pattern, a predetermined distance along the length. Each of the flutes has at least one tooth with each tooth having a crest and a base adjacent the flute. The pattern of the grooves can follow a first helical path along its length. The helical path can be substantially constant over a major portion of its entire length, in relation to the axes or can have a constantly changing path. A second pattern can follow a second, contiguous helical path that has a second radial orientation to the axis.

The teeth can be formed from a sinusoidal wave form comprised of a continuous radius going from convex to concave, with each of the teeth having a predetermined pitch from the crest to the base. In another embodiment the crest the teeth on the first flute is offset axially by a predetermined distance from the teeth on the adjacent flutes. The offset can be determined by dividing the pitch on each flute by the number of flutes.

The cutting head can, in an alternate embodiment, have a notch within each of the flutes. The notch forms a pair of teeth, the crests of each of the teeth can have either a substantially equal radius or a different radius, depending upon the placement of the notch.

BRIEF DESCRIPTION OF THE DRAWINGS

The advantages and aspects of the present invention will be better understood with reference to the following detailed description of the preferred embodiments when read in conjunction with the following figures.

DETAILED DESCRIPTION OF THE PREFERRED EMBODIMENTS

Figure 1:
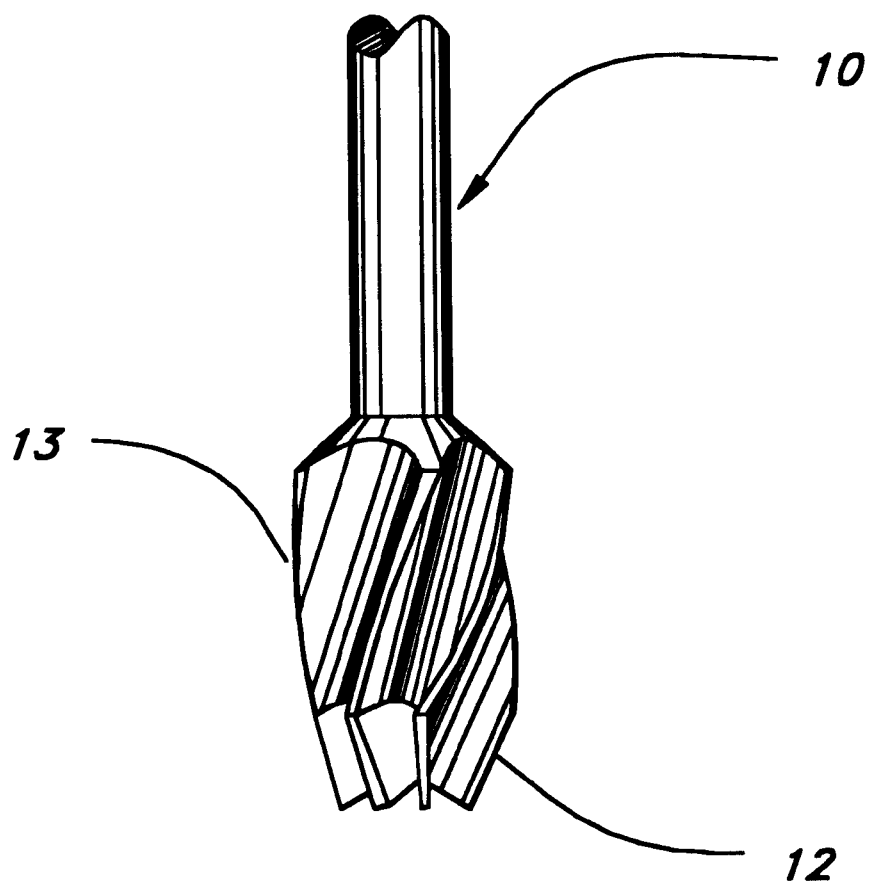
FIG. 1 is a prior art cutting head, as disclosed by Matthews et al, shown mounted on a flexible drive shaft.
Figure 2:
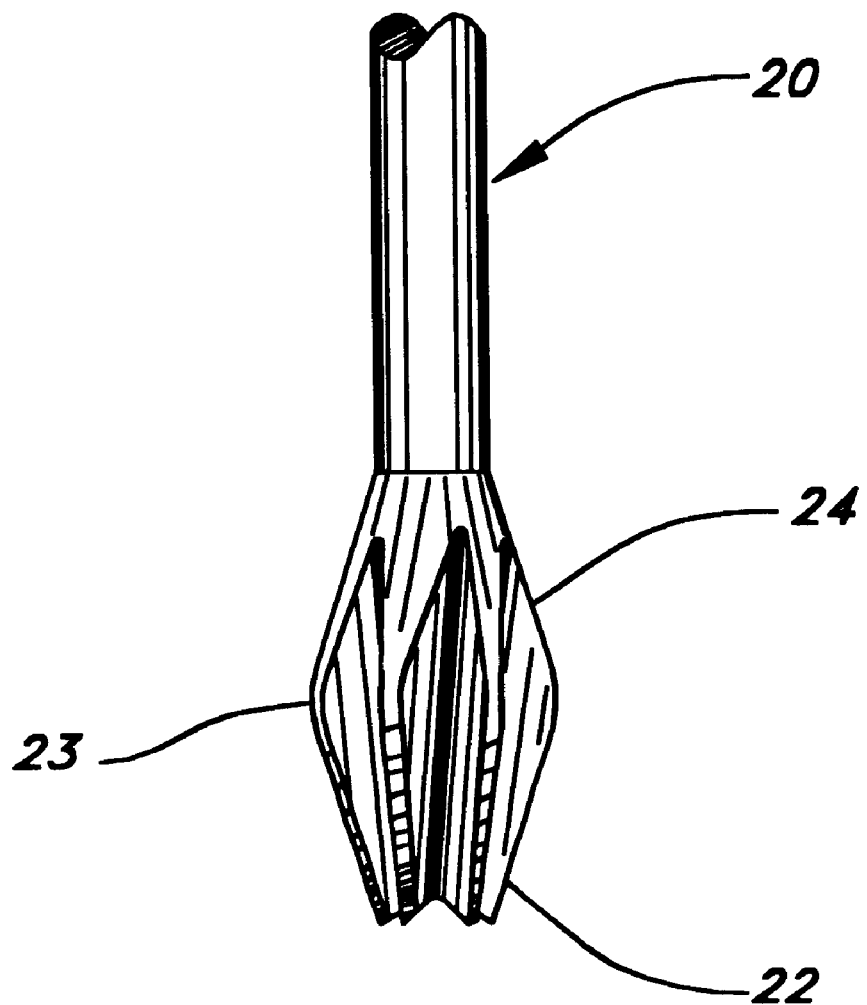
FIG. 2 is a prior art cutting head as disclosed by Borzone et al, shown mounted on a flexible drive shaft.

FIG. 1 illustrates the prior art cutting head as disclosed in U.S. Pat. No. 4,706,659, and indicated generally as 1.01. The prior art cutting head 1.01 has a conical shaped leading end 1.02 and a generally cylindrical trailing end 1.03. Another prior art cutting head is illustrated in FIG. 2, as disclosed in U.S. Pat. No. 5,122,134, and generally denoted as 2.01. The '134 cutting head 2.01 has conical shaped leading edge 2.02 and a generally elliptical mid-section 2.03 and a conical shaped trailing edge 2.04.

These prior art cutting devices have the problems that they create substantially heat as they cut. To reduce the force required and the heat generated, the prior art devices increase the diameter of each cutting head by small increments, generally about 0.05 mm. The disclosed cutting head reduces friction through the use of teeth along each of the flutes, thereby decreasing the force required and heat generated.

Figure 3:
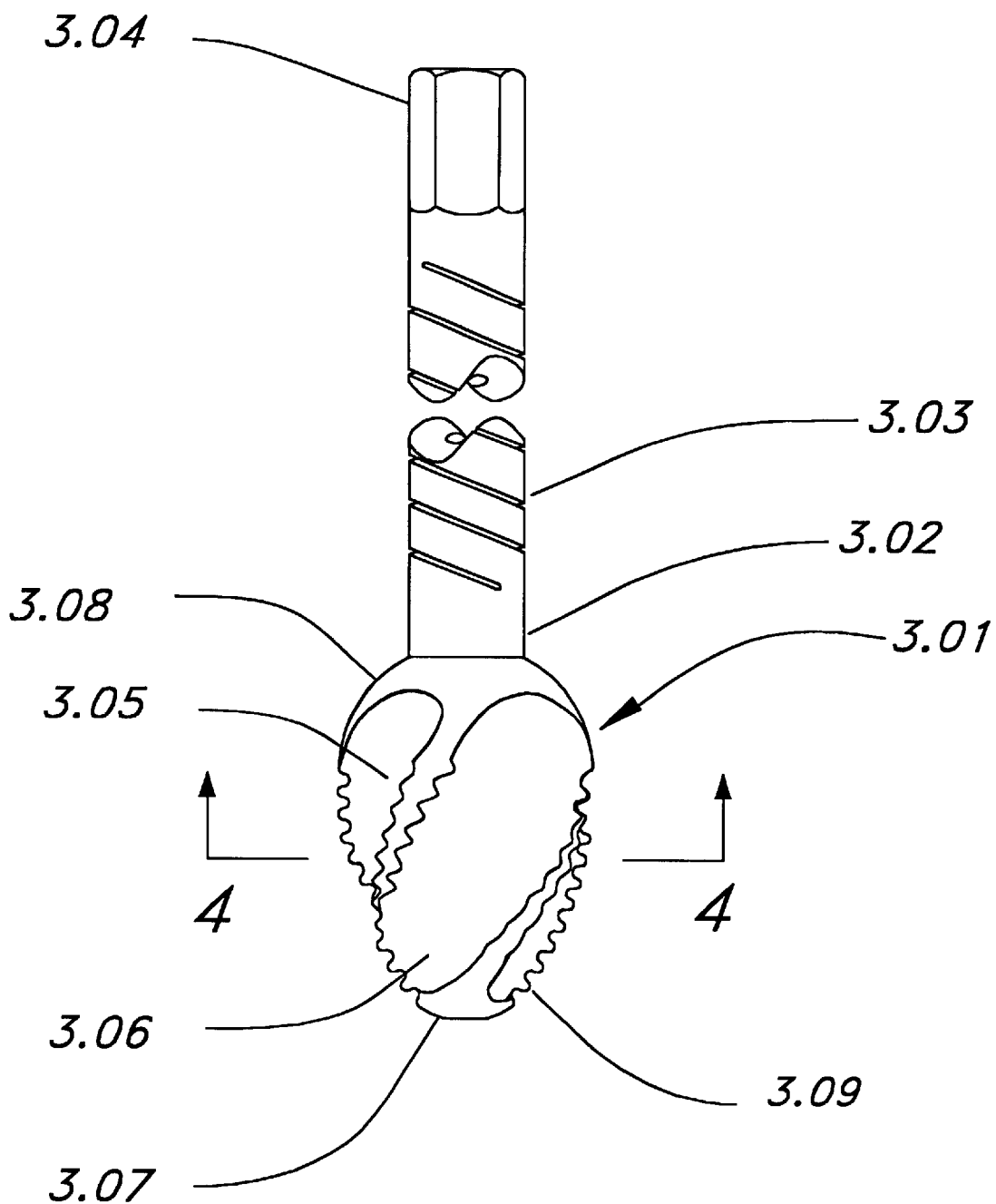
FIG. 3 is a side view of the cutting head of the present invention, shown mounted on a flexible shaft.

FIG. 3 shows a cutting head of the present invention generally denoted as 3.01. As well known in the art, the cutting head 3.01 is rigidly connected to, or integral with, a drive shaft segment 3.02 which is coupled with, or integral to, a flexible shaft 3.03. The drive shaft 3.03 includes a drive connector 3.04 which can be connected to any suitable electrical or pneumatic power tool. The cutting head 3.01 of the present invention includes a plurality of flutes 3.05 separated by generally V-shaped grooves 3.06. that extend from a leading tip portion 3.07 to a trailing portion 3.08 about the axis of rotation.

The flutes 3.05 can extend around the cutting head 3.01 in a fixed helical fashion, or in a constant variable helix around the axis of rotation. Alternatively, the flutes can extend parallel to the axis. Each of the flutes 3.05 has a series of machined fine pitched teeth 3.09, beginning at the leading tip 3.07 and extended to the trailing portion 3.08.

Figure 3B:
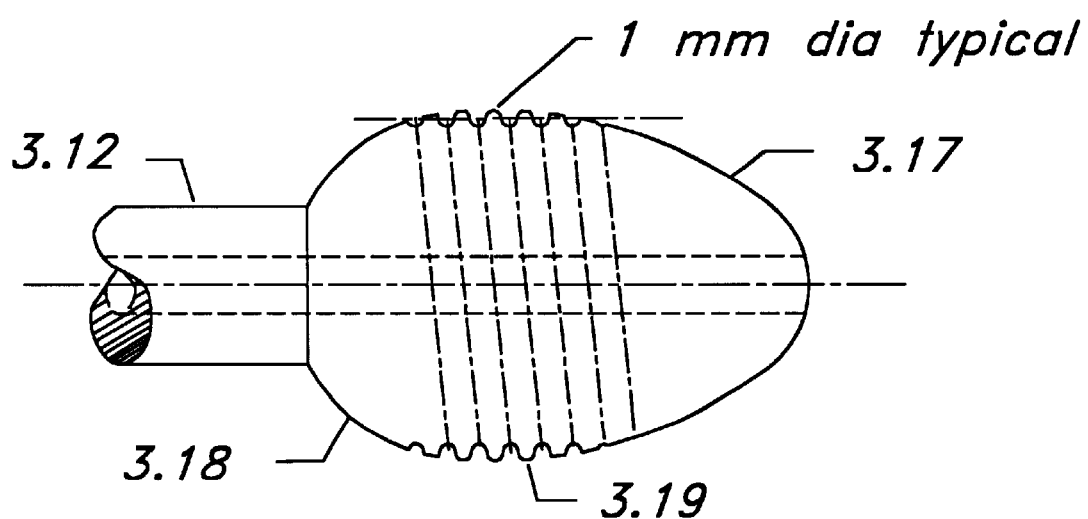
FIG. 3b is a side view of the cutting head of the present invention with a modified rougher segment.

Alternatively, the machining of the fine pitched teeth beginning anywhere between the leading tip and the major diameter of the cutter and extend to a predetermined point between the major diameter and the trailing portion. This is illustrated in the embodiment of FIG. 3b wherein the cutting head 3.18 has a series of fine pitched teeth 3.19 machined along the major diameter of the cutting head and in a plane parallel to the axis of rotation of the cutting head. Thus, the tip 3.17 of the cutting head 3.18 is void of the pitched teeth 3.19. This embodiment is easy to manufacture and provides no disadvantages during use.

Figure 4:
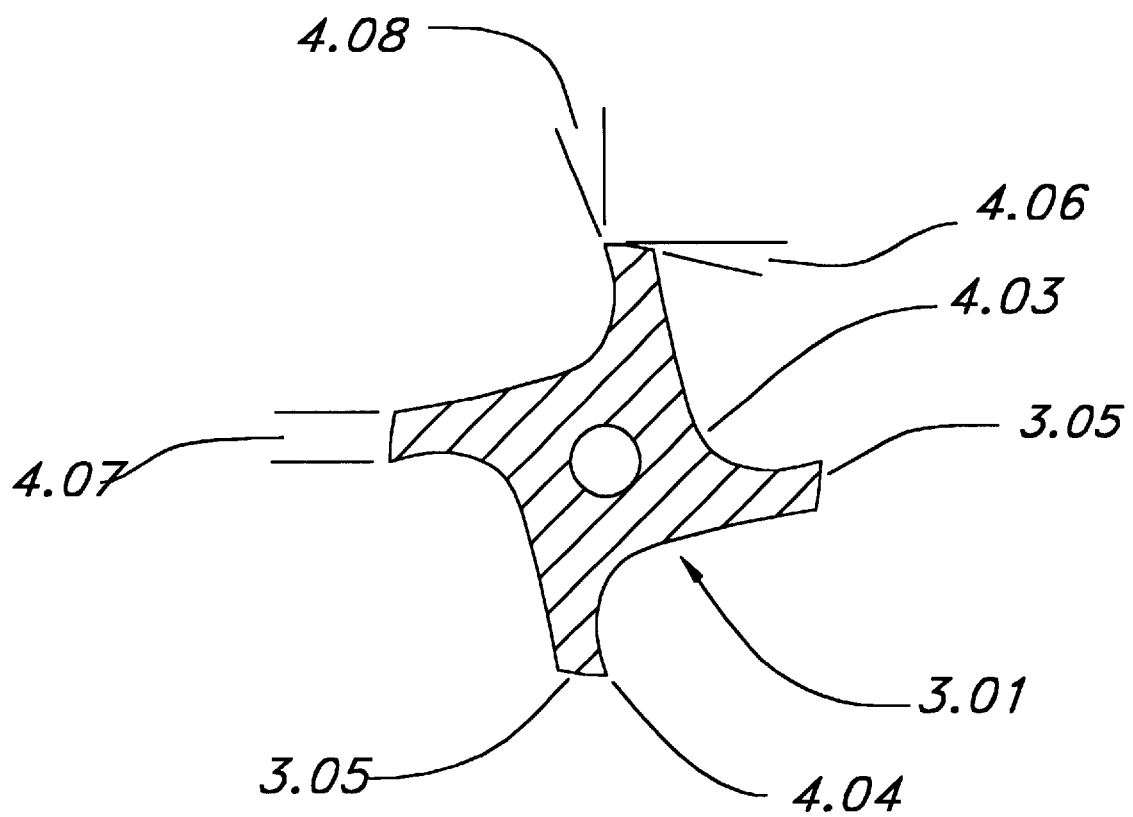
FIG. 4 is a cross-sectional view of the cutting head of the present invention along line 4—4 of FIG. 3.

The cross-sectional view 4—4 of the cutting bead 3.01 of FIG. 3 is illustrated in FIG. 4. This figure more clearly illustrates the plurality of flutes 3.05 formed by the V-shaped grooves 3.06, thereby creating the cutting edge 4.04 and a trailing edge 4.05. The V-shaped grooves 3.06 are machined in such a way as to provide a radial rake angle 4.08 to form the cutting edge 4.04. By varying the shape and location of this V-shaped groove 3.06 various radial rake angles, ranging from negative to positive, can be obtained. The variations and optimum angles are dependent upon use, equipment, etc., and will be known by those skilled in the art.

Each of the flutes 3.05 has a width 4.07 that is determined by end use and can be modified by reducing the size of the V-shaped grooves 306 or increasing the diameter of the head 3.01. The size adjustments will be evident to those skilled in the art. A relief angle 4.06 is formed on the width 4.07, or circumference, of each flute 3.05. The relief angle 4.06, generally in the range of about 0 to 15 degrees, is preferably formed on the flutes 4.02 by machining to remove the desired amount of material from the circumference of each of the cutter flutes 4.02. Alternatively, the head can be initially molded to incorporate the appropriate dimensioning.

Figure 5:
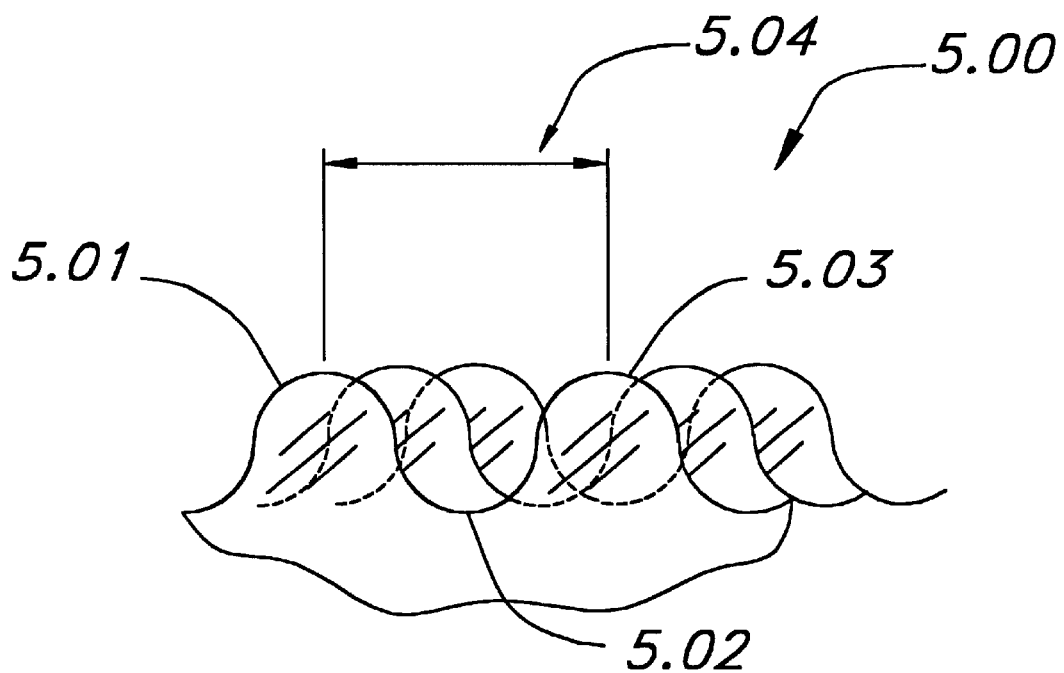
FIG. 5 is a detail of the rougher configuration, showing the staggered pitch of each successive cutting edge.

FIG. 5 is a schematic illustration of the pitch of the designs of the rougher teeth 5.00. In this embodiment, the rougher teeth 5.00 are designed with a sinusoidal or other wave form with a continuous radius going from a convex 5.01 to concave 5.02 to convex 5.03, etc. to produce fine pitch tooth like profile along the cutting edge of the flute. The distance from the crest of one convex tooth 5.01 to the next crest is known as the pitch 5.04. By varying the radius of the convex and concave portions of the sinusoidal wave, different pitches and size of rougher teeth 5.00 can be produced. Although generally, for ease of manufacture, the pitch will remain constant, the pitch can be varied from flute to flue or even tooth to tooth.

Figure 6:
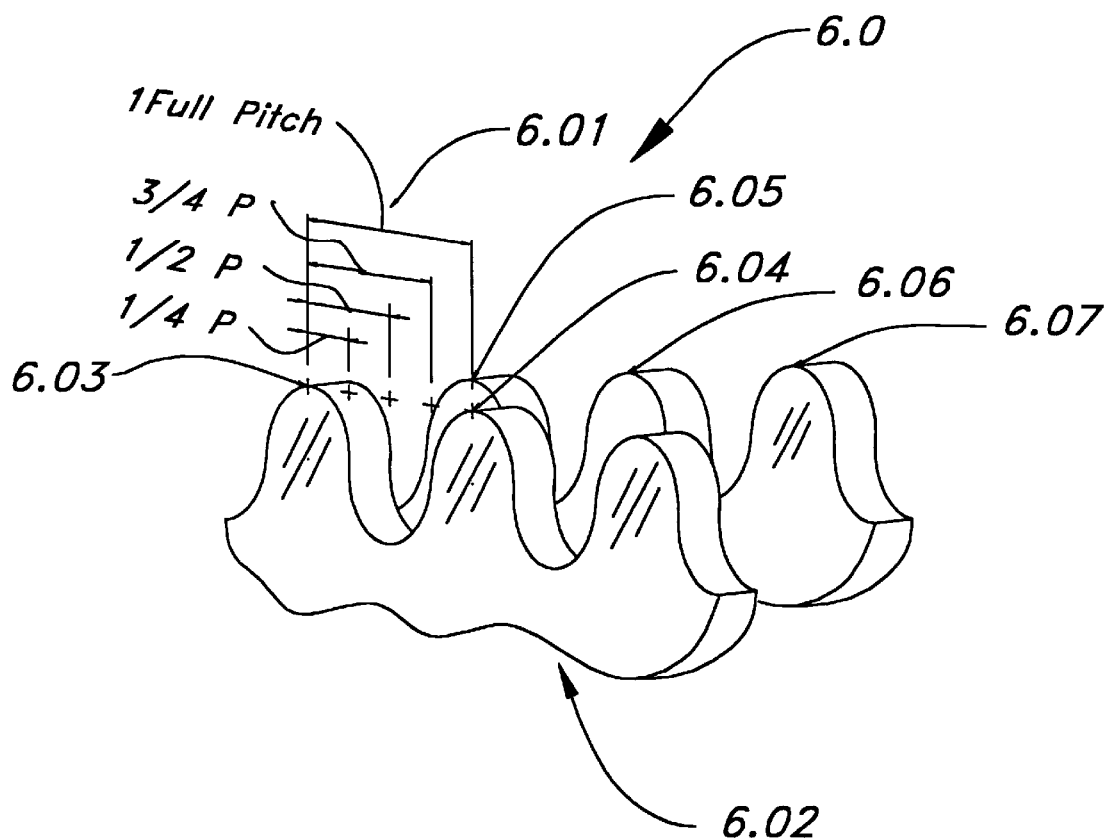
FIG. 6 is a detail of the rougher configuration of each cutting edge overlapping the path of the previous rougher cutting edge.

As shown in the embodiment of FIG. 6, the rougher teeth 6.00 are staggered axially along the flute edge such that the pitch 6.01 on each flute is equally divided by the total number of flutes on the cutter. The pitch 6.01 on the first flute 6.02 is shown with its start 6.03 on the crest of the first tooth and with the end of the pitch 6.04 on the crest of the second tooth. The pitch 6.01 is shown divided into 4 equal spaces, for example, the number of flutes on this cutter. The crest of the second succeeding flute 6.05 is located axially along the cutter at a position ¼ of the distance of the pitch 6.01. The crest of the third succeeding flute 6.06 is located axially along the cutter at a position ½ of the distance of the pitch 6.01. The crest of the fourth succeeding flute 6.07 is located axially along the cutter at a position ¾ of the distance of the pitch 6.01. Although four flutes are used in this example, it should be noted that as few as two flutes can be used. The number of flutes is dependent upon the diameter of the cutting head and the depth of the V-groove. For example, cutting heads with a small diameter will use two to four flutes, while a medium diameter cutting head will contain up to about 8 flutes. Additional flutes will be used in larger diameter cutting heads and the number of additional flutes will be dependent on the diameter and end use. The dimensioning, depth of grooves and number of flutes will be evident to those skilled in the art.

Figure 7:
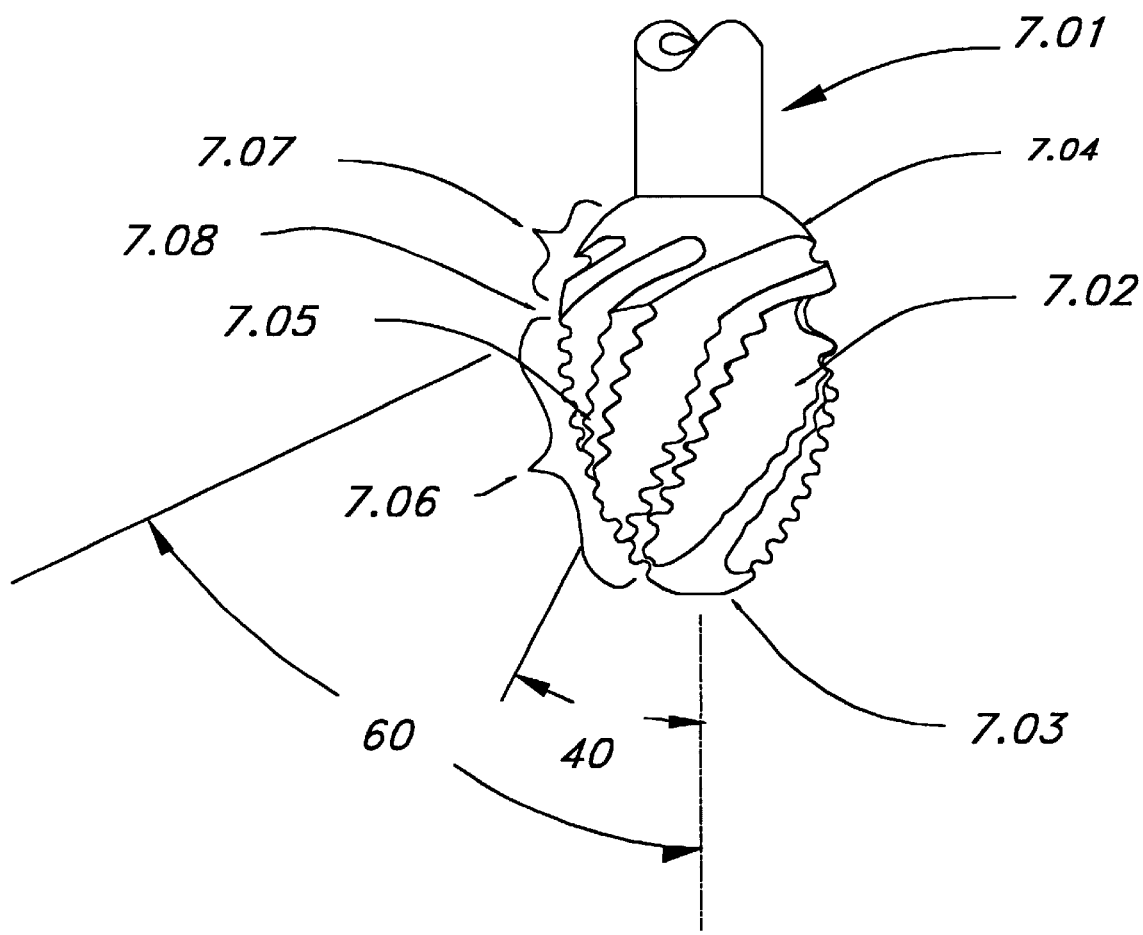
FIG. 7 is a side view of the cutting head of the present invention showing the variable helix angle.

Referring to FIG. 7, there is shown a cutting head 7.01 of the present invention that uses a variable helix angle within the head 7.01. In this preferred embodiment, a plurality of flutes 7.05 are separated by V-shaped grooves 7.02 that extend from the leading tip portion 7.03 to a trailing portion 7.04. The flutes 7.05 in this embodiment are machined with variable helix angles that, for purposes of illustration, are indicated by low helix section 7.06 and high helix section 7.07. It should be noted that in order to provide a clear, unobstructed path, the helix angles are formed by varying the machine angle of the slots 7.02. The low helix angle section 7.06 has a starting point at the leading end 7.03 and extends a predetermined axial distance towards the trailing end 7.04. The high helix angle section 7.07 progresses axially from the low helix end point 7.08 and extends axially towards and ending at the trailing end 7.04. The helix angles shown herein are 40 degrees and 60 degrees but any variation and combination of helix angles, from 0° to <90° can be used. Using a low helix angle, ranging from 0 up to 45 degrees, along the low helix section 7.03 will prevent the tendency of the cutter from catching and pulling into the bone. This high helix angle will clear the chips and debris from the cutter and act to prevent the chips from moving back into the bone on retraction of the cutter.

Figure 8:
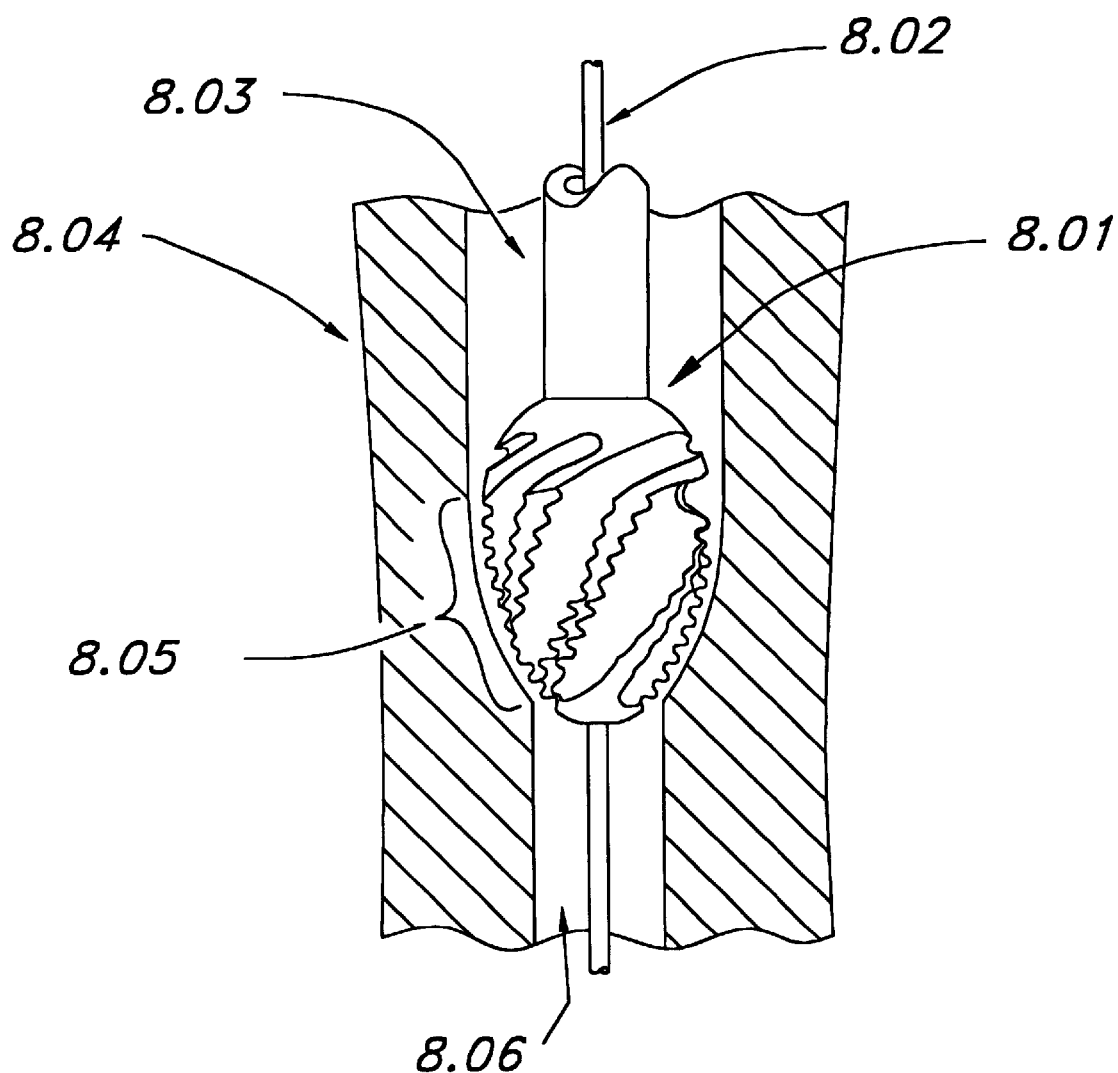
FIG. 8 is a side view of the cutting head of the present invention mounted on a flexible shaft reaming the medullary canal of a femur shown in cross section.

FIG. 8 shows a side view of the cutter head 8.01 of the present invention being passed over a guide wire 8.02, inserted into the intramedullary canal 8.06 of a long bone 8.04. As can be seen in the Figure, as the cutter head 8.01 progresses along the guide wire 8.02, the bore 8.03 the intramedullary canal 8.06 is enlarged. The roughing teeth on the flutes generate smaller chips, thereby reducing the torque required as well as heat generated by the cutting action.

Figure 9:
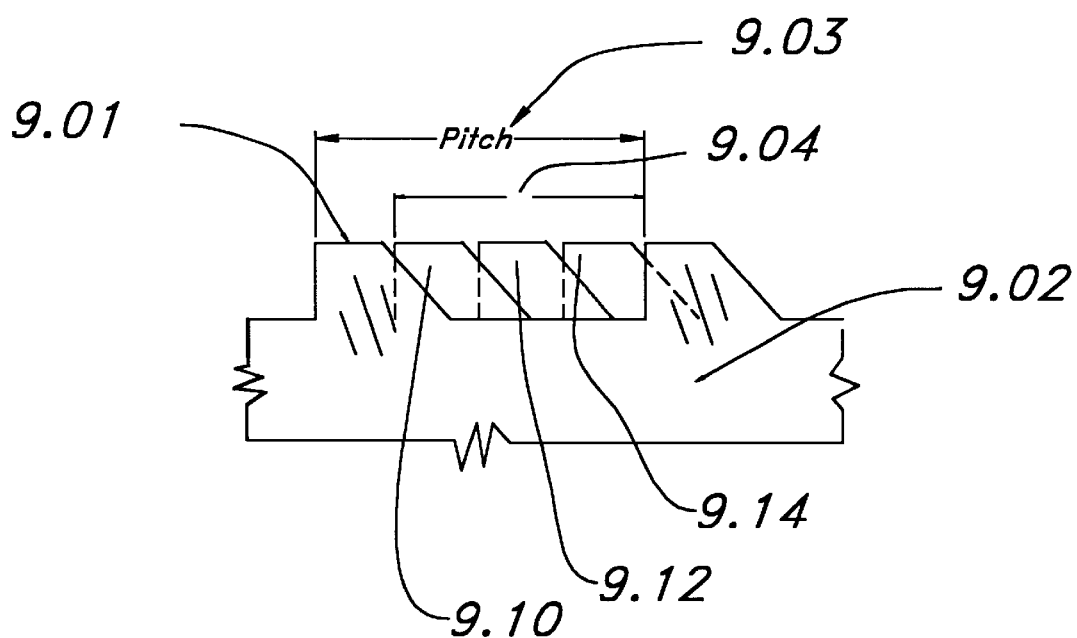
FIG. 9 is a fragmentary view of another embodiment of the rougher configuration illustrated in FIG. 6, showing each cutting edge overlapping the path of the previous rougher cutting edge.
Figure 10:
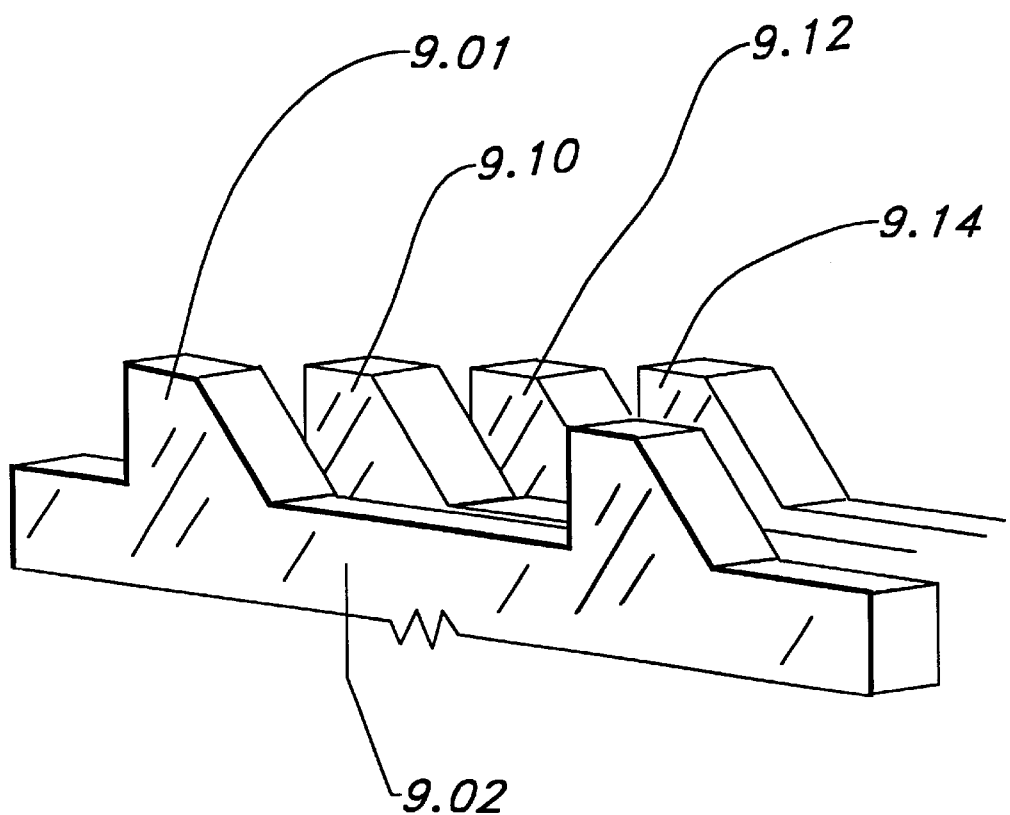
FIG. 10 is a fragmentary cross-sectional view of another embodiment of the rougher configuration of FIG. 7, showing the stagger of the pitch of the cutting edges.

Referring to FIGS. 9 and 10, there is shown a variation of the roughing teeth 6.00 shown in FIG. 6. On the cutting edge 9.01 of the flute 9.02, there is a series of machined grooves located a predetermined axial distance or pitch 9.03. On subsequent flutes the cutting edges 9.10, 9.12 and 9.14 are offset as disclosed heretofore. The groove area 9.04 configuration can be formed in various ways utilizing, straight edges and sharp angles, or radius corners and curved surfaces.

Figure 11:
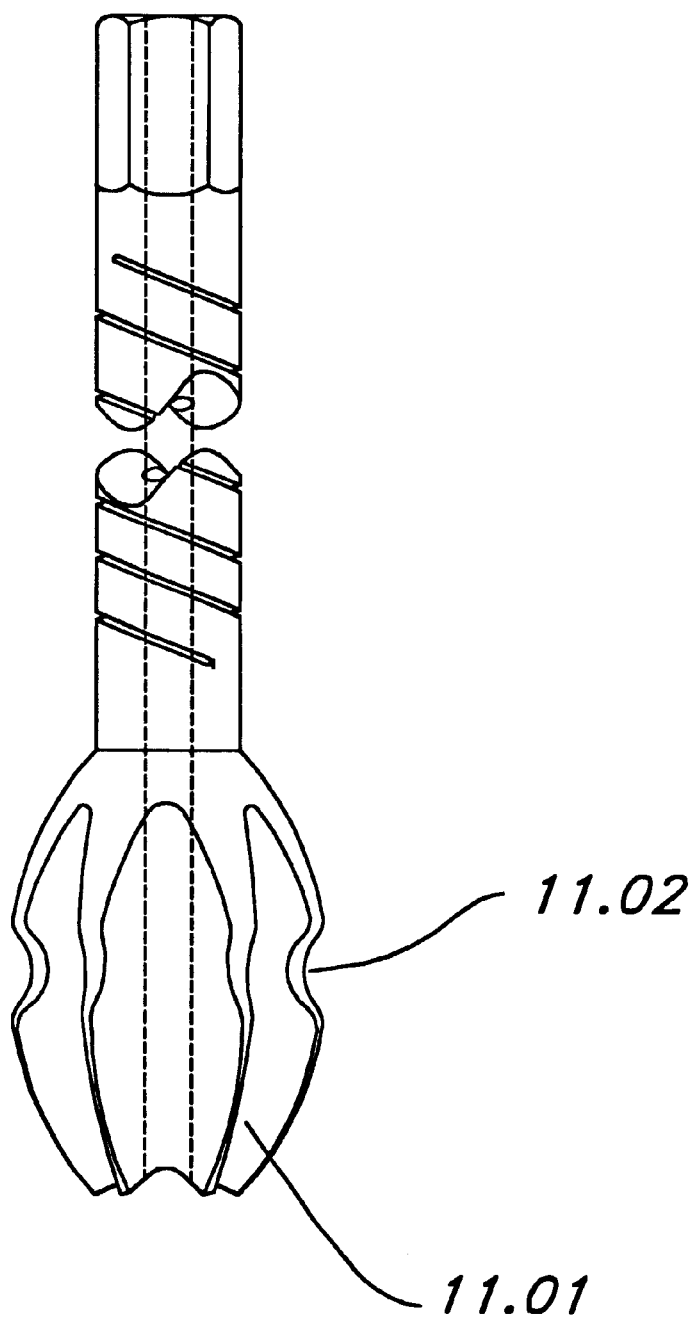
FIG. 11 is a side view of a still further embodiment of a cutting head, the cutting head having a recession along the arc of the profile.
Figure 12:
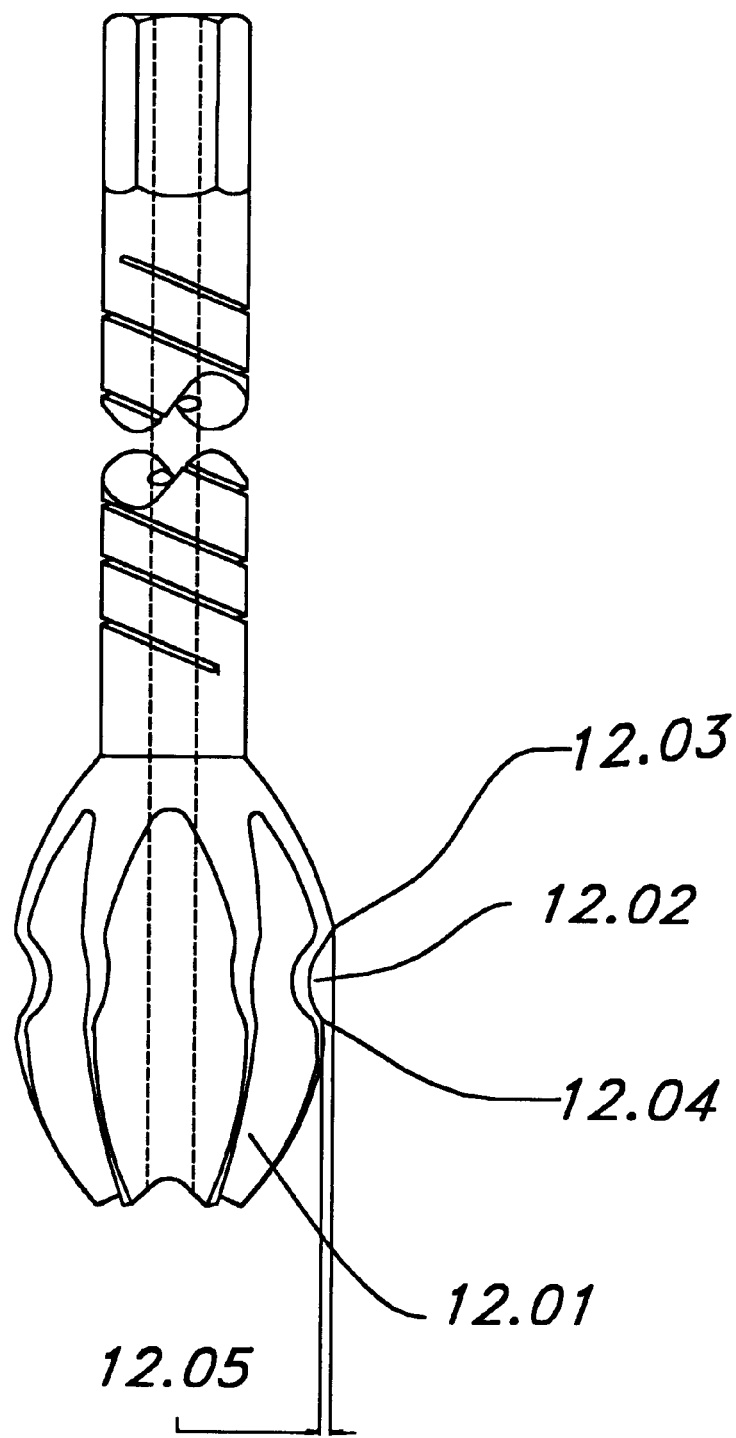
FIG. 12 is a side view of a further embodiment of a cutting head of the present invention, the cutting head having a recession toward the leading end, below the arc of the profile.

In FIG. 11, the cutting head 11.01 of the present invention has a notched section 11.02 in each of the flutes to form the cutting edges, or teeth. This single notch serves to break down the bone chips into small pieces, as noted herein. In the cutting head 11.01 of FIG. 11, the notch is centered within the length of the cutter 11.01, at the point of maximum diameter. In FIG. 12, the notch 12.02 is moved toward the leading tip creating teeth 12.03 and 12.01, each of which have a different radius. The crest of the tooth 12.03 will have a diameter, being at or about, the point of maximum diameter of the cutting head and have a larger diameter than the crest of the tooth 12.04. The difference between the crests of the two teeth 12.03 and 12.04 is shown herein as 12.05. The notches are formed by removing the material by machining or, alternatively the notches can be molded into the cutting head.

Figure 13:
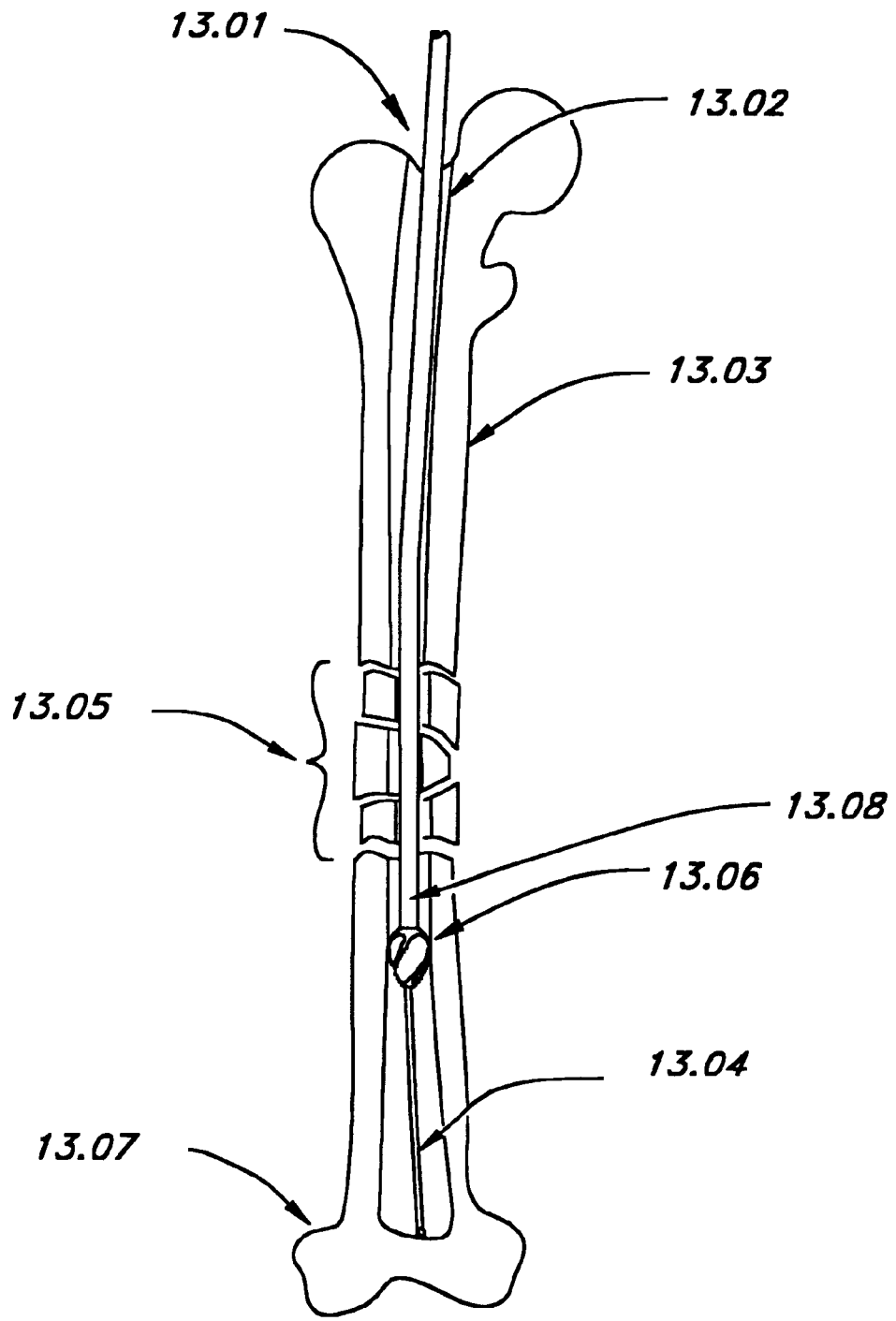
FIG. 13 is a side view of the invention being used in the medullary canal of a long bone such as a femur.

FIG. 13 shows a side view of a cutting head of the present invention inserted into the hip end 13.01 of the canal 13.02 of a long bone such as a femur 13.03. A guide wire 13.04 is initially inserted into the hip end 13.01 of the canal 13.02 and bridges the fracture area 13.05. The reamer cutter 13.06 and shaft 13.08 combination is inserted over the guide wire 13.04 and down the canal 13.02 towards the knee end 13.07, enlarging the canal 13.02 as it passing through the canal 13.02.

UTILIZATION AND OPERATION OF THE INVENTION

The utilization and operation of the preferred invention will be described with reference to the embodiments and descriptions of FIGS. 3, 8, and 13.

When a surgeon is required to enlarge the central canal 13.02 of a long bone such as the femur 13.03, he will usually start the process by making a small hole in the end of the bone at the area of the hip joint 13.01 with a pointed tool called an awl. A small diameter wire rod 13.04 is inserted into the hole and down the medullary canal 13.02 to the knee joint area 13.07. A small reamer 13.06 is selected and passed over the guide wire 13.04 and the reaming process begins. After the first reamer is passed through the canal and extracted, another reamer is selected and mounted on the shaft 13.08 or a complete assembly is selected. This process is repeated until the borehole is of sufficient width to insert the intramedullary fixation device or implant.

In the prior art systems, the next incremental size chosen is usually a reamer 0.5 mm larger, and repeating the process until a final bore is achieved. This process may mean changing reamers 9 to 10 times since the prior art reamer cutters utilize the small incremental diameter changes to reduce the size of the bone chips, torque loads and to reduce the heat generated by the cutting action against the canal wall.

Prior art cutters rely on a short cutting edge on each flute to cut the bone chips, cutting only four chips per revolution from the bone. These chips tend to be long fragments and must be passed along the V grooves of the cutter and out of the bone canal.

The disclosed invention utilizes the roughing teeth on the flutes to generate smaller chips, between 16 to 48 small chips per revolution. This cutting action reduces the torque required to cut the bone and creates smaller bone chips and debris and thus reduces the heat generated by the cutting action. The small bone fragments and debris are easily removed and can serve to benefit the healing process by filling in small voids in the fracture area to promote bone growth.

With the reduced torque loads and heat, cutter increments of from about 1 to about 2 mm can now be selected for reaming the canal. Further, since the design of the disclosed cutter enables a larger cutting length, the number of reamer interchanges is reduced from 8 or 10 to 3 or 4.

What is claimed is:

1. A cutting head for surgical reamers for use in enlarging the bore of the central medullary canal of a bone, said cutting head comprising:
   a. leading tip,
   b. a trailing end, said trailing end being connectable to a drive shaft, c. a length, said length being the distance from said leading tip to said trailing end, d. an asymmetrical longitudinal cross sectional circumference, said circumference increasing in diameter from said leading edge to a crest and decreasing from said crest to said trailing end, e. a plurality of grooves, said grooves extending in at least one pattern a predetermined distance along said length, thereby forming at least two flutes, each of said flutes having at least two teeth along at least a portion of a length of said flute, each tooth having a crest, said crest having a width equal to said width of said flute, whereby said cutting head asymmetrical longitudinal cross sectional circumference increases the interior diameter of bore hole as said cutting head progresses down said bore hole.

2. The cutting head of claim 1 wherein said crest of each of said teeth on one flute is off set axially by a predetermined distance from the crest of each of said teeth on an adjacent flute.

3. The cutting head of claim 2 wherein said at least one pattern of said grooves includes a first helical path along said length.

4. The cutting head of claim 3 wherein said first helical path has a first radial orientation to the axis, said orientation being substantially constant over a major portion of its entire length.

5. The cutting head of claim 3 wherein said at least one pattern of said grooves includes a second helical path along said length.

6. The cutting head of claim 5 wherein said first helical path has a first radial orientation to the axis, said orientation being substantially constant over a major portion of its entire length.

7. The cutting head of claim 2 wherein said at least two teeth are in the form of a sinusoidal wave.

8. The cutting head of claim 2 wherein each of said at least two teeth has a predetermined pitch from the crest of each of said teeth to the crest of each of said teeth.

9. The cutting head of claim 8 wherein said pitch of each of said teeth varies in a predetermined pattern.

10. The cutting head of claim 2 wherein said offset is determined by dividing the pitch on each flute by the number of flutes.

11. The cutting head of claim 1 wherein the crest of each of a first of said at least two teeth has a greater radius than the second of said at least two teeth.

12. A cutting head for surgical reamers for use in enlarging the bore of the central medullary canal of a bone, said cutting head comprising:

a. a leading tip, b. a trailing end, said trailing end being connectable to a drive shaft, c. a length, said length being the distance from said leading tip to said trailing end, d. an arced longitudinal cross sectional circumference, said circumference increasing in diameter from said leading tip to a crest and decreasing from said crest to said trailing end, e. a plurality of grooves, said grooves extending in at least one pattern a predetermined distance along said length, thereby forming at least two flutes, each of said flutes having at least two teeth along at least a portion of a length of said flute, each tooth having a crest, said crest having a width equal to said width of said flute, whereby said cutting head arced longitudinal cross sectional circumference increases the interior diameter of the bore hole as said cutting head progresses down said bore hole.

13. The cutting head of claim 12 wherein the crest of each of said at least two teeth has a substantially equal radius.

14. A surgical reamer for use in enlarging the bore of the central medullary canal of a bone, said surgical reamer having a cutting head, said cutting head having:

a. a leading tip, a. a trailing end, said trailing end being connectable to a drive shaft, b. a length, said length being the distance from said leading tip to said trailing end, c. an asymmetrical longitudinally cross sectional circumference, said circumference increasing in diameter from said leading tip to a crest and decreasing from said crest to said trailing end, d. a plurality of grooves, said grooves extending in at least one helical pattern a predetermined distance along said length, thereby form a plurality of flutes, each of said flutes having a plurality of evenly spaced teeth along at least a portion of said flute, each of said teeth having a crest and a base, the crest of each of said teeth on a first flute being off set axially at a predetermined pitch from the crest of each of said teeth on an adjacent flute, wherein said cutting head has an increasing curved surface along a longitudinal axis from said leading tip to a predetermined maximum circumference point and a decreasing curved surface from said maximum circumference point to said trailing end.

15. A method of enlarging the bore of the central medullary canal of a bone, comprising reaming said medullary canal with a surgical reamer, said surgical reamer having a cutting head, said cutting head having:

a leading tip, a trailing end, said trailing end being connectable to a drive shaft, a length, said length being the distance from said leading tip to said trailing end, an asymmetrical longitudinal cross sectional circumference, said circumference increasing in diameter from said leading tip to a crest and decreasing from said crest to said trailing end, a plurality of grooves, said grooves extending in at least one helical pattern a predetermined distance along said length, thereby form a plurality of flutes, each of said flutes having a plurality of evenly spaced teeth along at least a portion of said flute, each of said teeth having a crest and a base, the crest of each of said teeth on a first flute being off set axially at a predetermined pitch from the crest of each of said teeth on an adjacent flute, further comprising the steps of a. making a small hole in the end of the bone;

b. placing a first size of said cutting head on a reamer shaft;

c. enlarging said hole to a first stage;

d. removing said cutting head from said bone;

e. replacing said first size of said cutting head with a second size of said cutting head;

f. enlarging said hole to a second stage;

g. removing said cutting head from said bone;

h. repeating steps e–g until said hole is the appropriate size;

wherein said increasing curved surface of said cutting head enables said hole to be gradually enlarged from the diameter of said leading end to the diameter of said maximum circumference.

* * * * *